US012661351B2

(12) United States Patent
Shah et al.

(10) Patent No.: US 12,661,351 B2
(45) Date of Patent: Jun. 23, 2026

(54) STABLE LIQUID COMPOSITIONS OF POSACONAZOLE

(71) Applicant: INVENGENE PRIVATE LIMITED, Mumbai (IN)

(72) Inventors: Vaibhavi Shah, Mumbai (IN); Mayurbhai Sankalia, Vadodara (IN); Pradnya Borhade, Kalwa (IN)

(73) Assignee: INVENGENE PRIVATE LIMITED, Mumbai (IN)

( * ) Notice: Subject to any disclaimer, the term of this patent is extended or adjusted under 35 U.S.C. 154(b) by 653 days.

(21) Appl. No.: 17/928,460

(22) PCT Filed: Jun. 4, 2021

(86) PCT No.: PCT/IN2021/050542
§ 371 (c)(1),
(2) Date: Nov. 29, 2022

(87) PCT Pub. No.: WO2021/245703
PCT Pub. Date: Dec. 9, 2021

(65) Prior Publication Data
US 2023/0285391 A1 Sep. 14, 2023

(30) Foreign Application Priority Data
Jun. 6, 2020 (IN) .............................. 202021023774

(51) Int. Cl.
| | |
|---|---|
| *A61K 31/496* | (2006.01) |
| *A61K 9/00* | (2006.01) |
| *A61K 9/08* | (2006.01) |
| *A61K 47/18* | (2017.01) |
| *A61K 47/40* | (2006.01) |

(52) U.S. Cl.
CPC .............. *A61K 31/496* (2013.01); *A61K 9/08* (2013.01); *A61K 47/183* (2013.01); *A61K 47/40* (2013.01)

(58) Field of Classification Search
CPC ...... A61K 31/496; A61K 9/08; A61K 47/183; A61K 47/40; A61K 9/0019
See application file for complete search history.

(56) References Cited

U.S. PATENT DOCUMENTS

| | | | |
|---|---|---|---|
| 5,567,817 A | 10/1996 | Ray et al. | |
| 5,707,975 A | 1/1998 | Francois et al. | |
| 6,407,079 B1 | 6/2002 | Muller et al. | |
| 6,632,803 B1 | 10/2003 | Harding | |
| 9,023,790 B2 | 5/2015 | Heimbecher et al. | |
| 2004/0092527 A1 | 5/2004 | Bharatrajan et al. | |
| 2007/0082870 A1 | 4/2007 | Buchanan et al. | |
| 2011/0224232 A1 | 9/2011 | Williams, III et al. | |
| 2016/0008358 A1 | 1/2016 | Kulkarni et al. | |

FOREIGN PATENT DOCUMENTS

| | | | | |
|---|---|---|---|---|
| CN | 1259916 C | 7/2000 | | |
| CN | 1596897 A | 3/2005 | | |
| CN | 1294912 C | 9/2005 | | |
| CN | 1686136 A | 10/2005 | | |
| CN | 1788725 A | 6/2006 | | |
| CN | 102499909 B | 6/2012 | | |
| CN | 102670490 A | 9/2012 | | |
| CN | 103230363 A | 8/2013 | | |
| CN | 103690968 A | 4/2014 | | |
| CN | 103860457 A | 6/2014 | | |
| CN | 103284959 A | 6/2015 | | |
| CN | 106265534 A | 1/2017 | | |
| CN | 106511262 A | 3/2017 | | |
| CN | 108187069 B | 3/2019 | | |
| EP | 0575976 A1 | 12/1993 | | |
| EP | 2018866 A1 | 1/2009 | | |
| EP | 2467379 B1 | 3/2016 | | |
| EP | 2720723 B1 | 4/2018 | | |
| IN | 2232/MUM/2014 | 1/2016 | | |
| IN | 4944/CHE/2015 | 7/2017 | | |
| KR | 1020140130881 A | 11/2014 | | |
| WO | WO-2012005973 A1 * | 1/2012 | .............. | A61P 35/04 |
| WO | 2013026694 A1 | 2/2013 | | |
| WO | 2014108918 A2 | 7/2014 | | |

OTHER PUBLICATIONS

NOXAFIL® (posaconazole) injection, for intravenous use, USFDA Labeling-Package Insert, Jan. 20, 2022.
Macaev et al., Recent Advances in the Use of Cyclodextrins in Antifungal Formulations, Current Topics in Medicinal Chemistry, 2013, 13, pp. 2677-2683.
Tang et al., Posaconazole/hydroxypropyl-β-cyclodextrin host-guest system: Improving dissolution while maintaining antifungal activity, Tang et al., Carbohydrate Polymers vol. 142, May 20, 2016, pp. 16-23.
Carneiro et al., Cyclodextrin-Drug Inclusion Complexes: In Vivo and In Vitro Approaches, International Journal of Molecular Sciences, 2019, 20, 642, pp. 1-23.
Cristina et al., Influence of cyclodextrin on posaconazole stability, release and activity: Improve the utility of the drug, Journal of Drug Delivery Science and Technology, vol. 53, Oct. 2019, 101153.
Tan et al., Characterization and In Vitro Evaluation of the Complexes of Posaconazole with β- and 2,6-di-O-methyl-β-cyclodextrin, AAPS PharmSciTech, vol. 18, No. 1, Jan. 2017.
Abdel-Rahman et al., Single-Dose Pharmacokinetics of Intravenous Itraconazole and Hydroxypropyl-B-Cyclodextrin in Infants, Children, and Adolescents, Antimicrobial Agents and Chemotherapy, Aug. 2007, pp. 2668-2673.

* cited by examiner

*Primary Examiner* — Bruck Kifle
*Assistant Examiner* — Kevin S Martin

(57) ABSTRACT

The present invention relates to stable, room-temperature storable, liquid compositions comprising posaconazole. The liquid compositions, when stored at room temperature conditions, exhibit no significant coloration and no significant loss in chemical stability. The liquid compositions also exhibit good dilution stability with no evidence of precipitation. The present invention also provides a process for the preparation of such liquid compositions.

15 Claims, No Drawings

STABLE LIQUID COMPOSITIONS OF POSACONAZOLE

FIELD OF THE INVENTION

The present invention relates to stable, room-temperature storable, liquid compositions of posaconazole. The invention further provides a process for preparation of the said compositions.

BACKGROUND OF THE INVENTION

Posaconazole is a potent broad-spectrum azole antifungal agent useful in the treatment of invasive fungal infections. Posaconazole is administered parenterally for prophylaxis of invasive *aspergillus* and *candida* infections, in patients who are at high risk of developing these infections due to being severely immunocompromised such as hematopoietic stem cell transplant recipients with graft-versus-host disease or those with hematologic malignancies with prolonged neutropenia from chemotherapy.

Posaconazole is a weakly basic drug with poor aqueous solubility. Posaconazole is partially solubilized in strong acidic (aqueous) solutions of pH 1 or lower, where it has a solubility of about 790 mcg/ml. In contrast, at pH>4, posaconazole has a solubility of less than 1 mcg/ml in aqueous solutions. Although the solubility increases under acidic conditions, a more dramatic increase in solubility would be required to meet the projected daily intravenous dosage of more than 100 mg.

Commercially available parenteral posaconazole (NOXAFIL®) is an injection in the form of a solution containing posaconazole, sulfobutylether beta-cyclodextrin (SBECD), edetate disodium, hydrochloric acid, sodium hydroxide and water for injection. The said injection contains posaconazole and SBECD in a weight ratio of 1:22.3. The solution has a pH of around 2.6. The said injection has to be stored at refrigerated conditions of 2-8° C. (36-46° F.).

U.S. Pat. No. 9,023,790 relates to aqueous solutions of posaconazole for intravenous administration. These compositions contain sulfobutylether-beta-cyclodextrin (SBECD) as a solubilizing agent, in an acidified solution, and a chelating agent such as disodium edetate (EDTA). Stability screening studies showed that the said posaconazole solutions underwent color changes on storage. The development of color was minimized by inclusion of EDTA. A storage temperature of 5° C. further minimized the development of yellow color.

Indian Patent Application 4944/MUM/2015 relates to stable parenteral pharmaceutical formulation comprising posaconazole, cyclodextrin, buffering agents and/or pH-adjusting agents and one or more solvents, wherein the pH of the formulation ranges from about 4 to 8. Exemplified embodiments of posaconazole solutions (Examples 1, 2), in the said patent application, contain posaconazole at a concentration of 18 mg/ml. Other examples are related to freeze dried compositions.

Chinese Patent Publication No. 106265534 relates to a lyophilized powder for injection comprising posaconazole, a cyclodextrin, a metal ion chelating agent and a pH regulator, and a preparation method thereof.

Chinese Patent No. 103284959 relates to lyophilized powder injection and a preparation method thereof. The powder injection comprises active ingredient posaconazole, a solubilizing cyclodextrin and a pH adjuster, prepared using a process that uses a mix of organic solvents and water for injection.

One of the main concerns with posaconazole liquid compositions is that they are prone to coloration. According to prior art U.S. Pat. No. 9,023,790 aqueous solutions of posaconazole have been found to become pale yellow coloured within two weeks of storage at 4° C., 25° C. and 60% RH, and 40° C. and 75% RH, the yellow colour growing darker with time.

Another concern with posaconazole liquid compositions is the increased chances of degradation of the drug when stored at room temperature conditions, or at accelerated temperature conditions, in accordance with ICH guidelines.

Yet another concern with liquid compositions containing a drug such as posaconazole, which has poor and pH-dependent solubility, is the precipitation of the drug from its liquid composition when diluted with infusion fluids for parenteral administration.

Commercially available posaconazole parenteral solutions need to be stored at refrigerated conditions of 2-8° C. (36-46° F.) throughout their shelf life, to reduce coloration and chemical degradation, and to prevent precipitation.

Maintaining refrigerated conditions during transport and storage of pharmaceutical products during their shelf life requires cold-chain infrastructure which can be unreliable, expensive and not feasible. Failure to maintain cold-chain conditions can compromise the quality of the product at the point of use.

Further, commercially available posaconazole parenteral solutions contain stabilizers like EDTA to reduce coloration, and chemical degradation. Stabilizers like EDTA have been reported to lead to anaphylactic reactions, kidney damage and kidney failure.

It has surprisingly been found that the liquid compositions of posaconazole of the present invention exhibit good storage stability over extended periods of time at room temperature conditions, without the need for storage at refrigerated conditions. The liquid compositions, on storage at room temperature conditions, exhibit no significant coloration and no significant loss in chemical stability. The liquid compositions also exhibit good dilution stability with no evidence of precipitation.

Thus, the major advantage of the posaconazole liquid compositions of the present invention is that it eliminates the need for refrigeration, and special handling and/or storage requirements.

Further, the adequate storage stability of the liquid compositions of posaconazole, at room temperature conditions, can be achieved even without the use of stabilizers.

OBJECTS OF THE INVENTION

The principal object of the present invention is to provide liquid compositions of posaconazole, the said liquid compositions being stable and storable, at room temperature conditions (i.e. 25° C.±2° C., or 25° C.±2° C. and 60±5% relative humidity, or 30° C.±2° C. and 60±5% relative humidity).

Another object of the present invention is to provide liquid compositions of posaconazole, the said liquid compositions being stable and storable at room temperature conditions, with no significant coloration.

Yet another object of the present invention is to provide stable, room-temperature storable, liquid compositions comprising posaconazole, and hydroxypropyl beta-cyclodextrin.

Yet another object of the present invention is to provide liquid compositions of posaconazole which are free of stabilizers, the said liquid compositions being stable and storable, at room temperature conditions.

Yet another object of the present invention is to provide stable, room-temperature storable, liquid compositions of posaconazole, which exhibit the desired dilution stability.

Yet another objective of the present invention is to provide liquid compositions of posaconazole for parenteral administration.

Yet another objective of the present invention is to provide liquid compositions of posaconazole for parenteral administration, the said liquid compositions being in the form of a solution.

Yet another objective of the present invention is to provide liquid compositions of posaconazole for oral administration.

Yet another objective of the present invention is to provide liquid compositions of posaconazole for oral administration, the said liquid composition being in the form of a solution.

Yet another objective is to provide a process for the preparation of the said liquid compositions.

SUMMARY OF THE INVENTION

The present invention relates to stable, room-temperature storable, liquid compositions comprising posaconazole. The compositions, preferably in the form of solutions, can be administered orally or parenterally. The present invention also provides a process for the preparation of such liquid compositions.

DETAILED DESCRIPTION OF THE INVENTION

Chemical degradation, coloration, and precipitation on dilution are the major challenges in the development of stable liquid compositions comprising posaconazole, such as posaconazole solutions. Commercially available posaconazole parenteral solutions need to be stored at refrigerated conditions of 2-8° C. (36-46° F.) throughout their shelf life, to reduce coloration and chemical degradation, and prevent precipitation on storage and dilution. Further, the solutions require the use of stabilizers like EDTA.

It has surprisingly been found that the posaconazole liquid compositions of the present invention exhibit adequate and desired storage stability at room temperature conditions, and do not require refrigerated storage conditions of 2-8° C. (36-46° F.) to achieve the desired shelf life of at least about 18 months. Further, the said storage stability at room temperature conditions can be achieved even without the use of a stabilizer like EDTA.

In addition, the said liquid compositions comprising posaconazole, such as posaconazole solutions, also exhibit desired dilution stability in infusion fluids, and do not show any precipitation, or render the diluted solution unusable for the desired purpose.

"Room temperature conditions" as used herein refers to 25° C.±2° C., or 25° C.±2° C. and 60%±5% relative humidity, or 30° C.±2° C. and 75%±5% relative humidity (RH). Room temperature refers to the temperature and/or humidity conditions prevailing in a work area, which range from 15° C. to 25° C.±2° C. and 60%±5% relative humidity for Mediterranean and subtropical climatic regions (Zone II of the ICH Stability Climatic Zone), to 30° C.±20° C. and 75%±5% relative humidity for hot and highly humid regions (Zone IVB of the ICH Stability Climatic Zone). These temperature and/or humidity ranges encompass the usual and customary working environment and temperatures that are generally experienced in pharmacies, hospitals, and warehouses, and during shipping, in these regions. ICH guidelines recommend conducting long-term storage stability studies at the "room temperature conditions" of the various zones to establish its stability and shelf-life.

"Room temperature storable" when used herein refers to liquid composition that can be stored at "room temperature" for at least a period of 6 months, without significant coloration, and without significant loss of chemical stability.

"Accelerated temperature conditions" as used herein refers to 40° C.±2° C. and 75%±5% relative humidity.

The degree of coloration of liquid compositions of posaconazole is determined using European Pharmacopeia (EP) Color Standards. These standards are visual color standards, intended to define a sample color as being close to a physical liquid standard (2.2.2 Degree of Coloration of Liquids, European Pharmacopoeia). The test is carried out by comparing the test solution with a standard color solution, when viewed down the vertical axis of the tubes, in diffused light, against a white background. In the present invention, EP Color Standard BY (brownish-yellow) solutions are used as a reference to determine the coloration of posaconazole liquid compositions.

"Coloration" as used herein means a degree of coloration more intense than BY4, preferably more intense than BY5, and more preferably more intense than BY6.

"Chemical stability" as used herein means that the content of posaconazole, as determined by an HPLC assay method, is not less than 90% of the label claim, and the percent total impurities, as determined by an HPLC method, is not more than 2%.

The liquid compositions of posaconazole can be in the form of solutions, suspensions, colloids, or emulsions. Preferably, the liquid compositions of posaconazole are in the form of a solution.

In an aspect of the invention, the liquid compositions may be dried using processes such as spray-drying, fluid bed drying, or freeze drying (lyophilisation) to provide powders. The said powder can be reconstituted with liquid vehicles to provide solutions, suspensions, colloids, or emulsions.

The liquid compositions of posaconazole, of the present invention, can be administered orally or parenterally.

The room temperature storable liquid compositions of posaconazole of the present invention exhibit the desired chemical stability and no coloration, when stored at room temperature conditions over extended periods of time.

In one aspect, the posaconazole liquid composition of the present invention is stable at room temperature conditions for at least 18 months.

In another aspect, the room temperature storable liquid compositions of posaconazole, comprise posaconazole, hydroxypropyl beta-cyclodextrin (HPBCD), and a vehicle.

In another aspect, the room temperature storable liquid compositions of posaconazole, consist essentially of posaconazole, hydroxypropyl beta-cyclodextrin, and a vehicle.

In another aspect, the room temperature storable liquid compositions comprise posaconazole, hydroxypropyl beta-cyclodextrin, and water as the vehicle.

In another aspect, the room temperature storable liquid compositions comprise posaconazole, hydroxypropyl beta-cyclodextrin, sodium edetate, and water as the vehicle.

In another aspect, the room temperature storable liquid compositions comprise posaconazole, hydroxypropyl beta-cyclodextrin, sodium edetate, and water as the vehicle.

In yet another aspect, the room temperature storable liquid compositions comprise posaconazole, hydroxypropyl beta-cyclodextrin, and a vehicle, the said liquid compositions being free of stabilizers.

Liquid compositions of posaconazole contain posaconazole in concentrations ranging from about 10 mg/ml to about 30 mg/ml, preferably from about 15 mg/ml to about 30 mg/ml, and more preferably from about 18 mg/ml to about 30 mg/ml of the said liquid composition.

Liquid compositions of posaconazole contain about 1.0% w/v to about 3.0% w/v, preferably about 1.5% w/v to about 3.0% w/v, and more preferably about 1.8% w/v to about 3.0% w/v of posaconazole.

Liquid compositions of posaconazole comprise hydroxypropyl beta-cyclodextrin in concentrations ranging from about 100 mg/ml to about 500 mg/ml, preferably from about 150 mg/ml to about 450 mg/ml, and more preferably from about 200 mg/ml to about 400 mg/ml, and most preferably from about 250 mg/ml to about 350 mg/ml, of the said liquid composition.

In one aspect, the said liquid compositions comprise posaconazole and hydroxypropyl beta-cyclodextrin, in a weight ratio ranging from about 1:5 to about 1:30, preferably from about 1:5 to about 1:25 and more preferably from about 1:10 to about 1:25.

In another aspect, the said liquid compositions comprise posaconazole and hydroxypropyl beta-cyclodextrin, in a molar ratio ranging from about 1:5 to about 1:25, preferably from about 1:5 to about 1:20 and more preferably from about 1:5 to about 1:15.

One or more vehicles in the liquid compositions of posaconazole are selected from aqueous vehicles such as water for injection, alcohols (such as ethyl alcohol), glycols (such as propylene glycol, butylene glycol, glycerol, polyethylene glycol), dioxalanes, dimethylacetamide, hydroxyethyl lactamide, dimethylsulfoxide, and non-aqueous vehicles like polyoxyethylated castor oils, oils (such as corn oil, cottonseed oil, sesame oil, peanut oil), fixed oils, ethyl oleate, isopropyl myristate, and benzyl benzoate. Preferably, the vehicle in the posaconazole liquid compositions of the present invention is water for injection.

Posaconazole liquid compositions may further comprise excipients selected from anti-oxidants, chelating agents, pH-adjusting agents, buffering agents, and tonicity agents.

Anti-oxidants are selected from those known in the art such as butylated hydroxyanisole, butylated hydroxytoluene, propyl gallate, sodium metabisulfite, sodium sulfite, sodium bisulfite, citric acid, ascorbic acid or mixtures thereof.

Chelating agents are selected from those known in the art such as ethylenediaminetetraacetic (EDTA), ethylenediamine-N, N'-diacetic-N, N'-dipropionic acid, diethylenetriaminepentaacetic acid (DTPA), ethylene glycol-bis(beta-aminoethyl ether)-tetraacetic acid (EGTA), N-(hydroxy ethyl)ethylenediaminetriacetic acid (HEDTA), and nitrilotriacetic acid (NTA), or salts thereof. The term EDTA as used herein includes ethylenediaminetetraacetic acid, its salts, hydrates, solvates and derivatives, such as disodium ethylenediaminetetraacetic acid (disodium edetate), disodium ethylenediaminetetraacetic acid dihydrate (disodium edetate dihydrate), sodium calcium ethylenediaminetetraacetic acid (sodium calcium edetate), and tetrasodium ethylenediaminetetraacetic acid (tetrasodium edetate). In an aspect, chelating agents such as EDTA act as stabilizers and prevent coloration of posaconazole liquid compositions.

pH-adjusting agents can be acid or base. The base can be oxides, hydroxides, carbonates, bicarbonates and the like. The oxides can be metal oxides such as calcium oxide, and magnesium oxide; hydroxides can be of alkali metals and alkaline earth metals such as sodium hydroxide, potassium hydroxide, and calcium hydroxide; and carbonates can be sodium carbonate, sodium bicarbonates, and potassium bicarbonates. The acid can be mineral acids or organic acids such as hydrochloric, nitric, phosphoric, acetic, citric, sulfuric, fumaric, maleic, malic, tartaric, methanesulfonic, naphthalenesulfonic, p-toluenesulfonic, lactic, ascorbic acid, and glycine hydrochloride.

Buffering agents are selected from those known in the art and can be citrates, acetates, phosphates, other organic buffers and the like.

Tonicity agents are selected from those known in the art and can be selected from ionic tonicity agents such as sodium chloride, potassium chloride, magnesium chloride or calcium chloride, or non-ionic tonicity agents such as glycerine, dextrose and mannitol.

pH of the posaconazole liquid compositions can range from pH 2 to pH 4, preferably from pH 2.5 to pH 3.5, more preferably from pH 2.8 to pH 3.2.

Posaconazole liquid compositions of the present invention are stable and storable at room temperature conditions for extended periods of time, with no coloration, and no significant chemical degradation. The said liquid compositions do not require refrigerated conditions for storage.

Storage stability of the liquid compositions of the present invention was evaluated by subjecting the liquid compositions to storage at the following conditions for various time periods:

Room temperature conditions: 25° C.±2° C., or 25° C.±2° C. and 60%±5% RH, or 30° C.±2° C. and 75%±5% RH, Accelerated temperature conditions: 40° C.±2° C. and 75%±5% RH The compositions were analyzed for posaconazole content, percent known impurity (hydroxy triazole, deshydroxy posaconazole, benzylated posaconazole), and percent total impurities, after the time period.

In one aspect of the invention, the content of posaconazole in the liquid compositions, after storage at room temperature conditions for at least 3 months, is not less than 90%, preferably not less than 95% and more preferably not less than 98% of the label claim.

In another aspect of the invention, the content of posaconazole in the liquid compositions, after storage at room temperature conditions, for at least 6 months, is not less than 90%, preferably not less than 95% and more preferably not less than 98% of the label claim.

In another aspect of the invention, the content of posaconazole in the liquid compositions, after storage at room temperature conditions, for at least 12 months, is not less than 90%, preferably not less than 95% and more preferably not less than 98% of the label claim.

In another aspect of the invention, the content of posaconazole in the liquid compositions, after storage at room temperature conditions, for at least 18 months, is not less than 90%, preferably not less than 95% and more preferably not less than 98% of the label claim.

In another aspect of the invention, the content of posaconazole in the liquid compositions, after storage at room temperature conditions, for at least 22 months, is not less than 90%, preferably not less than 95% and more preferably not less than 98% of the label claim.

In another aspect of the invention, the content of posaconazole in the liquid compositions, after storage at room temperature conditions, for at least 24 months, is not less than 90%, preferably not less than 95% and more preferably not less than 98% of the label claim.

In yet another aspect of the invention, the content of posaconazole in the liquid compositions, after storage at accelerated temperature conditions, for at least 3 months, is not less than 90%, preferably not less than 95% and more preferably not less than 98% of the label claim.

In yet another aspect of the invention, the content of posaconazole in the liquid compositions, after storage at accelerated temperature conditions for at least 6 months, is not less than 90%, preferably not less than 95% and more preferably not less than 98% of the label claim.

In one aspect of the invention, the known impurity (hydroxy triazole, deshydroxy posaconazole, or benzylated posaconazole) in the liquid composition, after storage at room temperature conditions for at least 18 months, or accelerated temperature conditions for at least 6 months, is not more than 0.5%, preferably not more than 0.3% and more preferably not more than 0.2%.

In another aspect of the invention, the total impurities in the liquid composition, after storage at room temperature conditions for at least 18 months, or accelerated temperature conditions for at least 6 months, is not more than 2%, preferably not more than 1.5% and more preferably not more than 1%.

In an embodiment, the total impurities in the liquid composition, after storage at room temperature conditions, for at least 18 months, is not more than 0.8%.

In another embodiment, the total impurities in the liquid composition, after storage at room temperature conditions, for at least 18 months, is not more than 0.5%.

In one aspect the posaconazole liquid compositions for parenteral administration, when filled in vials, are chemically stable after storage in the upright orientation, at room temperature conditions, or accelerated temperature conditions, for various time periods as discussed above.

In another aspect the posaconazole liquid compositions for parenteral administration, when filled in vials, are chemically stable after storage in the inverted orientation, at room temperature conditions, or accelerated temperature conditions, for various time periods as discussed above.

Posaconazole liquid compositions of the present invention exhibit no coloration at room temperature conditions, after storage for extended periods of time for at least up to about 18 months.

In one aspect of the invention, the posaconazole liquid compositions of the present invention, show a coloration not more intense than BY6 after storage at room temperature conditions for at least 3 months.

In another aspect, the posaconazole liquid compositions of the present invention, show a coloration not more intense than BY6, after storage at room temperature conditions for at least 6 months.

In another aspect, the posaconazole liquid compositions of the present invention, show a coloration not more intense than BY5, after storage at room temperature conditions for at least 18 months.

In another aspect, the posaconazole liquid compositions of the present invention, show a coloration not more intense than BY4, after storage at room temperature conditions for at least 20 months.

In another aspect of the invention, the posaconazole liquid compositions of the present invention, show a coloration not more intense than BY6 after 3 months of storage at accelerated temperature conditions.

In another aspect of the invention, the posaconazole liquid compositions of the present invention, show a coloration not more intense than BY4 after 6 months of storage at accelerated temperature conditions.

Compositions of posaconazole in the form of solutions, for parenteral administration to a patient, may have to be aseptically diluted with a suitable infusion fluids before administration. Compositions on dilution with infusion fluids, are prone to precipitation of posaconazole from the composition, as posaconazole is a drug having poor and pH-dependent solubility.

In one aspect, the liquid compositions of posaconazole for parenteral administration are stable to dilution. The said solutions, after dilution with infusion fluids, are clear and do not show precipitation or turbidity for at least 24 hours, preferably at least 48 hours. The posaconazole solutions are stable to dilution ratios of upto about 1:30, preferably upto about 1:25, more preferably upto about 1:20 in infusion fluids.

Suitable infusion fluids are selected from those known in the art such as 5% dextrose solution in water, 0.45% sodium chloride solution in water, 0.9% sodium chloride solution in water, 5% dextrose and 0.45% sodium chloride solution in water, 5% dextrose and 0.9% sodium chloride solution in water and 5% dextrose and 20 mEq potassium chloride solution in water.

Liquid compositions of posaconazole, in the form of solutions for parenteral administration, were evaluated for tonicity using a Freezing Point Osmometer (Osmomat 3000) using 0.9% sodium chloride solution as the standard. Commercially available posaconazole parenteral solutions exhibit hyper-tonicity, with an osmolality greater than 2000 mOsmol/kg. Hence, commercially available posaconazole parenteral solutions have to be administered after dilution in infusion liquids, and cannot be administered as an intravenous bolus injection.

In an aspect, posaconazole liquid compositions of the present invention have an osmolality ranging from about 200 mOsmol/kg to about 800 mOsmol/kg, preferably from 200 mOsmol/kg to about 700 mOsmol/kg, more preferably from 200 mOsmol/kg to about 600 mOsmol/kg, and most preferably from 200 mOsmol/kg to about 500 mOsmol/kg.

In an aspect, posaconazole liquid compositions of the present invention having an osmolality ranging from about 200 mOsmol/kg to about 500 mOsmol/kg, can be injected as a bolus without dilution with infusion fluids.

In an embodiment, the liquid composition comprising posaconazole, hydroxypropyl beta-cyclodextrin and a vehicle, is stable at room-temperature for at least 18 months, preferably for at least 20 months, more preferably for at least 22 months, and most preferably for at least 24 months.

In another embodiment, the liquid composition comprising posaconazole, hydroxypropyl beta-cyclodextrin, and water as a vehicle, is stable at room-temperature for at least 18 months, preferably for at least 20 months, more preferably for at least 22 months, and most preferably for at least 24 months.

In yet another embodiment, the liquid composition comprising posaconazole, hydroxypropyl beta-cyclodextrin and water as a vehicle, is free of stabilizers, and is stable at room-temperature for at least 18 months, preferably for at least 20 months, more preferably for at least 22 months, and most preferably for at least 24 months.

In an aspect, the liquid compositions comprising posaconazole, have a room temperature shelf-life of at least 18 months, preferably of at least 20 months, more preferably of at least 22 months and most preferably of at least 24 months.

In another aspect, the liquid compositions comprising posaconazole, have a room temperature shelf-life of at least 24 months, in accordance with ICH guidelines.

In an embodiment, the liquid composition for parenteral administration, comprising posaconazole, is stable at room temperature conditions for at least 18 months, preferably for at least 20 months, more preferably for at least 22 months, and most preferably for at least 24 months.

In another embodiment, the liquid composition for parenteral administration, comprising posaconazole and hydroxypropyl beta-cyclodextrin, is stable at room temperature conditions for at least 18 months, preferably for at least 20 months, more preferably for at least 22 months, and most preferably for at least 24 months.

In yet another embodiment, the liquid composition for parenteral administration, comprising posaconazole, hydroxypropyl beta-cyclodextrin and a vehicle, is stable at room temperature conditions for at least 18 months, preferably for at least 20 months, more preferably for at least 22 months, and most preferably for at least 24 months.

In an embodiment, the room-temperature storable liquid composition comprises posaconazole, hydroxypropyl beta-cyclodextrin, and at least one vehicle.

In another embodiment, the room-temperature storable liquid composition comprises posaconazole, hydroxypropyl beta-cyclodextrin, and water as the vehicle.

In yet another embodiment, the room-temperature storable liquid composition, comprising posaconazole, hydroxypropyl beta-cyclodextrin, and water as the vehicle, is free of stabilizers The present invention also deals with a method of stabilizing posaconazole liquid composition, wherein the method comprises dissolving posaconazole in HPBCD solution, and adjusting the pH of the posaconazole-HPBCD solution to about 2 to 4, and wherein the posaconazole liquid composition is stable at room temperature conditions for at least 18 months.

The liquid compositions of posaconazole of the present invention are prepared by processes such as dissolving/dispersing posaconazole, HPBCD and/or other excipients in a vehicle, homogenization, adjusting the pH using pH-adjusting agents, sparging liquid with non-oxygen containing gas, adding vehicle to obtain the final volume, filtering the liquid composition, filling the liquid composition in a container, sealing the container, and/or sterilizing the liquid composition.

Processes for the preparation of liquid compositions of posaconazole for parenteral administration is preferably carried out under an overlay of a non-oxygen containing gas such as nitrogen.

In one of the embodiments of the present invention, the posaconazole liquid composition is prepared by a process comprising steps of:

(i) sparging water with a non-oxygen containing gas;

(ii) dissolving HPBCD, and at least one optional excipients selected from anti-oxidants, chelating agents, pH-adjusting agents, buffering agents and/or tonicity agents, in water sparged with non-oxygen containing gas, to obtain a HPBCD solution;

(iii) acidifying HPBCD solution to pH 1-2 using hydrochloric acid;

(iv) dissolving posaconazole in acidified HPBCD solution, to obtain a posaconazole solution;

(v) adjusting the pH of the posaconazole solution to pH 2-4 by adding sodium hydroxide and/or hydrochloric acid;

(vi) adding water to posaconazole solution and mixing it, to obtain the final batch volume, wherein the process steps (ii) to (vi) are carried out under an overlay of a non-oxygen containing gas.

In another embodiment, the posaconazole liquid composition is processed using one or more of the following steps:

(i) posaconazole liquid composition is filtered through a filter (ii) posaconazole liquid composition is filled in containers (iii) headspace of the container is overlayed with a non-oxygen containing gas (iv) the container is capped (v) the container is sealed In another embodiment, liquid composition of posaconazole, in the form of a solution, was prepared using the following manufacturing process:

HPBCD, and optionally excipients selected from anti-oxidants, chelating agents, pH-adjusting agents, buffering agents and/or tonicity agents, was added to and dissolved in water (sparged with nitrogen) to provide a clear HPBCD solution. HPBCD solution was acidified to pH 1-2 using hydrochloric acid. Posaconazole was added and dissolved in the acidified HPBCD solution to obtain a clear posaconazole solution. Additional sodium hydroxide or hydrochloric acid was added to the solution to adjust the pH of the posaconazole solution to pH 2-4. Water was added to obtain the final volume. The process of preparation of the solution was carried out under nitrogen overlay.

Liquid compositions of posaconazole, for parenteral administration, can be sterilized by dry heat sterilization, moist heat sterilization, chemical sterilization, radiation sterilization, and filtration sterilization. Filtration sterilization is one of the preferred methods of sterilization, as the method provides liquid compositions of posaconazole with the lowest degree of coloration, when compared to liquid compositions subjected to moist heat sterilization.

Filter materials used in the sterilization of liquid compositions include but are not limited to nylon, polycarbonate, cellulose acetate, polyvinylidene fluoride (PVDF), and polyethersulfone (PES). Pore sizes of the filters may range from 0.1 microns to 5 microns.

Liquid compositions of posaconazole are filled in containers which include vials, bottles, ampoules, cartridges, flexible bags and pre-filled syringes. The said containers maybe made of glass or plastic, or any other suitable material.

The invention is now illustrated with non-limiting examples.

Example 1

Disodium ethylene diamine tetraacetic acid dihydrate (sodium edetate) (0.18 g) was dissolved in 450 ml of water (sparged with nitrogen) under stirring. HPBCD (380.0 g) was added to the sodium edetate solution and continuously stirred till a clear solution was obtained. The pH was adjusted to about 1.5-2.0 using hydrochloric acid. Posaconazole (18.0 g) was added to the sodium edetate-cyclodextrin solution and continuously stirred till a clear solution was obtained. The pH was adjusted to about 2.3-2.8 using sodium hydroxide or hydrochloric acid. Water (sparged with nitrogen) was added to obtain the final volume (1000 ml), and mixed to obtain a posaconazole liquid solution. The process of preparation of the solution was carried out under nitrogen overlay.

The solution was filtered through 0.22 micron PVDF filter, and filled in sterilized vials (10 ml USP Type 1 Fiolax clear glass vial). The vial headspace was overlayed with nitrogen, the vials stoppered using 20 mm bromobutyl fluorocarbon coated rubber stopper and sealed using 20 mm aluminium flip-off seals having PP disc.

Example 2

HPBCD (380.0 g) was added to 450 ml of water (sparged with nitrogen) and stirred continuously, optionally heating it to 65° C., till a clear solution was obtained. Posaconazole (18.0 g) was added to the cyclodextrin solution, with optional heating to 70° C., and continuous stirring. The pH was adjusted to about 2.4-2.7 using hydrochloric acid. Water (sparged with nitrogen) was added to obtain the final volume (1000 ml), and mixed to obtain a posaconazole liquid solution. The process of preparation of the solution was carried out under nitrogen overlay.

The solution was filtered through 0.22 micron PVDF filter, and filled in sterilized vials (10 ml USP Type 1 Fiolax clear glass vial). The vial headspace was overlayed with nitrogen, the vials stoppered using 20 mm bromobutyl fluorocarbon coated rubber stopper and sealed using 20 mm aluminium flip-off seals having PP disc.

Example 3

Disodium ethylene diamine tetraacetic acid dihydrate (sodium edetate) (0.18 g) was dissolved in 450 ml of water (sparged with nitrogen) under stirring. HPBCD (280.0 g) was added to the sodium edetate solution and stirred continuously till a clear solution was obtained. The pH was adjusted to about 1.6-1.9 using hydrochloric acid. Posaconazole (18.0 g) was added to the sodium edetate-HPBCD solution, and stirred continuously till a clear solution was obtained. The pH was adjusted to about 2.4-2.6 using sodium hydroxide or hydrochloric acid. Water (sparged with nitrogen) was added to obtain the final volume (1000 ml), and mixed, to obtain a posaconazole liquid solution. The process of preparation of the solution was carried out under nitrogen overlay.

The solution was filtered through 0.22 micron PVDF filter, and filled in sterilized vials (10 ml USP Type 1 Fiolax clear glass vial) at a fill volume of 16.7 ml. The vial headspace was overlayed with nitrogen, the vials stoppered using 20 mm bromobutyl fluorocarbon coated rubber stopper and sealed using 20 mm aluminium flip-off seals having PP disc.

Example 4

HPBCD (200.0 g) was added to 450 ml of water and continuously stirred till a clear solution was obtained. Tartaric acid (9.0 g) was added to the cyclodextrin solution. The pH was adjusted to about 1.6 using sodium hydroxide or hydrochloric acid. Posaconazole (10.0 g) was added to the HPBCD-tartaric acid solution and continuously stirred till a clear solution was obtained. The pH was adjusted to about 2.4 using sodium hydroxide or hydrochloric acid. Water was added to obtain the final volume (1000 ml), and mixed to obtain a posaconazole liquid solution. The process of preparation of the solution was carried out under nitrogen overlay.

The solution was filtered through 0.22 micron PVDF filter, and filled in sterilized vials (10 ml USP Type 1 Fiolax clear glass vial). The vial headspace was overlayed with nitrogen, the vials stoppered using 20 mm bromobutyl fluorocarbon coated rubber stopper and sealed using 20 mm aluminium flip-off seals having PP disc.

Evaluation of Posaconazole Liquid Compositions:
Degree of Coloration

Table 1 provides a comparison of the degree of coloration of aqueous solutions of commercially available posaconazole parenteral solution product, and posaconazole liquid compositions of examples 1, 3 and 4, after the said solutions were stored at room temperature conditions. The comparison was done using EP Color Standards of BY range.

TABLE 1

Degree of coloration of the commercially available product
and posaconazole solutions of examples 1, 3 and 4

| Sample | Degree of Coloration |
|---|---|
| Commercially available product | |
| 0 months | More intense than BY6 |
| 6 months (25° C. ± 2° C./ 60% ± 5% RH) | More intense than BY5 |
| Example 1 | |
| 0 month | Not more intense than BY7 |
| 6 months (25° C. ± 2° C./ 60% ± 5% RH) | Not more intense than BY6 |
| 6 months (30° C. ± 2° C./ 75% ± 5% RH) | Not more intense than BY6 |
| Example 3 | |
| 0 month | Not more intense than BY7 |
| 22 months (25° C. ± 2° C.) | Not more intense than BY5 |
| Example 4 | |
| 0 month | Not more intense than BY7 |
| 1 month (25° C. ± 2° C./ 60% ± 5% RH) | Not more intense than BY7 |

Chemical Stability

The chemical stability of posaconazole liquid compositions of examples 1, 2, and 3, on storage (upright and inverted positions) at room temperature conditions was studied by determining the posaconazole content and percent impurities of the liquid composition. The results are given in Tables 2, 3 and 4.

TABLE 2

Posaconazole content and % impurities of liquid compositions of
example 1 after storage at room temperature conditions
Example 1

| | Room Temperature Conditions (25° C. ± 2° C./60% ± 5% RH) | | | | | |
|---|---|---|---|---|---|---|
| | | Time-period of storage | | | | |
| Evaluation Parameter | Initial | 1M ↑ | 3M ↑ | 3M ↓ | 6M ↑ | 6M ↓ |
| % Assay | 102.2 | 99.8 | 100.3 | 99.0 | 102.5 | 102.2 |
| % Hydroxy Triazole | ND | ND | ND | ND | ND | ND |
| % Deshydroxy Posaconazole | ND | ND | 0.04 | 0.04 | 0.04 | 0.04 |
| % Benzylated Posaconazole | ND | ND | 0.02 | 0.03 | 0.02 | 0.03 |
| % Total Impurities | 0.14 | 0.07 | 0.26 | 0.27 | 0.12 | 0.13 |

TABLE 2-continued

| | Room Temperature Conditions (30° C. ± 2° C./75% ± 5% RH) | | | | | |
|---|---|---|---|---|---|---|
| | Time-period of storage | | | | | |
| Evaluation Parameter | Initial | 1M ↑ | 3M ↑ | 3M ↓ | 6M ↑ | 6M ↓ |
| % Assay | 102.2 | 97.4 | 98.2 | 98.6 | 101.8 | 100.9 |
| % Hydroxy Triazole | ND | ND | ND | ND | ND | ND |
| % Deshydroxy Posaconazole | ND | ND | 0.05 | 0.04 | 0.05 | 0.04 |
| % Benzylated Posaconazole | ND | ND | 0.02 | 0.02 | 0.03 | 0.03 |
| % Total Impurities | 0.14 | 0.07 | 0.29 | 0.28 | 0.13 | 0.17 |

ND = Not Detected;
M = Month(s);
'↑' = Upright Orientation of vial;
'↓' = Inverted Orientation of vial

TABLE 3

Posaconazole content and % impurities of liquid compositions
of example 2 after storage at room temperature conditions
Example 2

| | Time-period of storage | | | |
|---|---|---|---|---|
| Evaluation Parameter | Initial | 1M ↑ | 3M ↑ | 6M ↑ |
| Room Temperature Conditions (25°C ± 2° C. and 60% ± 5% RH) | | | | |
| % Assay | 98.0 | 101.6 | 100.4 | 100.5 |
| % Hydroxy Triazole | ND | ND | ND | ND |
| % Deshydroxy Posaconazole | 0.03 | ND | 0.02 | 0.03 |
| % Benzylated Posaconazole | 0.02 | ND | 0.02 | 0.03 |
| % Total Impurities | 0.05 | 0.18 | 0.07 | 0.33 |

ND =Not Detected;
M =Month(s);
'↑' =Upright Orientation of vial;
'↓' =Inverted Orientation of vial

TABLE 4

Posaconazole content and % impurities of liquid compositions of example 3 after
storage at room temperature conditions
Example 3

| | Time Period of Storage | | | | |
|---|---|---|---|---|---|
| Evaluation Parameter | Initial | 3M ↑ | 3M ↑ | 6M ↓ | 6M ↓ |
| Room Temperature Conditions (25° C. ± 2° C. and 60% ± 5% RH) | | | | | |
| % Assay | 100.3 | 99.3 | 101.6 | 99.3 | 101.6 |
| % Hydroxy Triazole | ND | ND | ND | ND | ND |
| % Deshydroxy Posaconazole | ND | 0.01 | 0.01 | 0.01 | 0.01 |
| % Benzylated Posaconazole | ND | ND | ND | ND | ND |
| % Total Impurities | 0.10 | 0.26 | 0.27 | 0.23 | 0.24 |
| Room Temperature Conditions (30° C. ± 2° C. and 75% ± 5% RH) | | | | | |
| % Assay | 100.3 | 98.7 | 99.4 | 102.4 | 103.0 |
| % Hydroxy Triazole | ND | ND | ND | ND | ND |
| % Deshydroxy Posaconazole | ND | 0.01 | 0.01 | 0.01 | 0.01 |
| % Benzylated Posaconazole | ND | ND | ND | ND | ND |
| % Total Impurities | 0.10 | 0.27 | 0.27 | 0.26 | 0.25 |

| | Time Period of Storage | | |
|---|---|---|---|
| Evaluation Parameter | Initial | 22M ↑ | 22M ↓ |
| Room Temperature conditions (25° C. ± 2° C.) | | | |
| % Assay | 100.3 | 101.3 | 103.0 |
| % Hydroxy Triazole | ND | ND | ND |

TABLE 4-continued

Posaconazole content and % impurities of liquid compositions of example 3 after
storage at room temperature conditions
Example 3

| | | | |
|---|---|---|---|
| % Deshydroxy Posaconazole | ND | 0.01 | 0.01 |
| % Benzylated Posaconazole | ND | ND | ND |
| % Total Impurities | 0.10 | 0.33 | 0.36 |

ND =Not Detected;
M =Month(s);
'↑' =Upright Orientation of vial;
'↓' =Inverted Orientation of vial The chemical stability of posaconazole liquid compositions of examples 1, 2, and 3, after storage (upright and inverted positions) at accelerated conditions was studied by determining the posaconazole content and percent impurities of the compositions. The results are given in Table 5, 6 and 7.

TABLE 5

Posaconazole content and % impurities of liquid compositions of
Example 1 after storage at accelerated temperature conditions
Example 1
Accelerated Temperature Conditions (40° C. ± 2° C. and 75% ± 5% RH)

| Evaluation Parameter | Time Period of Storage | | | | | | |
|---|---|---|---|---|---|---|---|
| | Initial | 1M ↑ | 1M ↓ | 3M ↑ | 3M ↓ | 6M ↑ | 6M ↓ |
| % Assay | 102.2 | 100.4 | 96.3 | 101.9 | 101.8 | 98.4 | 96.9 |
| % Hydroxy Triazole | ND | ND | ND | ND | ND | ND | ND |
| % Deshydroxy Posaconazole | ND | ND | ND | 0.04 | 0.04 | 0.04 | 0.05 |
| % Benzylated Posaconazole | ND | ND | ND | 0.02 | 0.02 | 0.03 | 0.03 |
| % Total Impurities | 0.14 | 0.11 | 0.11 | 0.41 | 0.42 | 0.37 | 0.43 |

ND = Not Detected;

M = Month(s);

'↑' = Upright Orientation of vial;

'↓' = Inverted Orientation of vial

TABLE 6

Posaconazole content and % impurities of liquid compositions of
Example 2 after storage at accelerated temperature conditions
Example 2

| Evaluation Parameter | Time Period of Storage | | | |
|---|---|---|---|---|
| | Initial | 1M ↑ | 3M ↑ | 6M ↓ |
| Accelerated Temperature Conditions (40°C ± 2° C./75% ± 5% RH) | | | | |
| % Assay | 98.0 | 98.5 | 101.0 | 100.2 |
| % Hydroxy Triazole | ND | ND | ND | 0.02 |
| % Deshydroxy Posaconazole | 0.03 | ND | 0.02 | 0.03 |
| % Benzylated Posaconazole | 0.02 | ND | 0.02 | 0.02 |
| % Total Impurities | 0.05 | 0.50 | 0.36 | 1.17 |

ND =Not Detected;
M =Month(s);
'↑' =Upright Orientation of vial;
'↓' =Inverted Orientation of vial

TABLE 7

Posaconazole content and % impurities of liquid compositions of
Example 3 after storage at accelerated temperature conditions
Example 3
Accelerated Temperature (40° C. ± 2° C. and 75% ± 5% RH)

| Evaluation Parameter | Time Period of Storage | | | | | | |
|---|---|---|---|---|---|---|---|
| | Initial | 1M ↑ | 1M ↓ | 3M ↑ | 3M ↓ | 6M ↑ | 6M ↓ |
| % Assay | 100.3 | 100.8 | 100.8 | 99.6 | 100.9 | 99.6 | 100.9 |
| % Hydroxy Triazole | ND | ND | ND | ND | ND | ND | ND |
| % Deshydroxy Posaconazole | ND | ND | ND | 0.01 | 0.01 | 0.01 | 0.01 |
| % Benzylated Posaconazole | ND | ND | ND | ND | ND | ND | ND |
| % Total Impurities | 0.10 | 0.26 | 0.27 | 0.37 | 0.38 | 0.50 | 0.41 |

ND = Not Detected;
M = Month(s);
'↑' = Upright Orientation of vial;
'↓' = Inverted Orientation of vial Dilution Studies and Tonicity Posaconazole liquid compositions of Examples 1, 2, 3 and 4 were diluted to a dilution ratio of 1:17 by mixing 1 ml of the liquid composition of the example and 17 ml of 0.9% sodium chloride solution in water. No precipitation or turbidity was observed in the diluted solution on storage at room temperature for 24 to 48 hours.

Posaconazole liquid compositions of Examples 1, 2, 3 and 4 were diluted to a dilution ratio of 1:17 by mixing 1 ml of the liquid composition of the example and 17 ml of 5% dextrose solution in water. No precipitation or turbidity was observed in the diluted solution on storage at room temperature for about 24 to about 48 hours.

The osmolality of the liquid compositions of Examples 1, 2 and 3 were determined to be 670 mOsmol/kg, 608 mOsmol/kg and 340 mOsmol/kg respectively, while the osmolality of the commercially available posaconazole solution for injection was found to be 2355 mOsmol/kg.

Thus, it has surprisingly been found that posaconazole liquid compositions of the present invention are room temperature storable. The said solutions exhibit good chemical stability and show no significant coloration, when stored at room temperature conditions for extended periods of time. The said liquid compositions of posaconazole exhibit good dilution stability, and exhibit an osmolality of about 200 mOsmol/kg to about 800 mOsmol/kg. The posaconazole liquid compositions comprise hydroxypropyl beta-cyclodextrin and a vehicle. Further, the said compositions are room temperature storable even without the inclusion of a stabilizer like EDTA.

We claim:

1. A posaconazole liquid composition, consisting essentially of:
(i) posaconazole at a concentration of about 15 mg/ml to about 30 mg/ml in the composition,
(ii) hydroxypropyl beta-cyclodextrin at a concentration of about 280 mg/ml to about 400 mg/ml in the composition, and
(iii) water as a vehicle,
wherein the composition is prepared by a process comprising:
(a) sparging water with nitrogen gas;
(b) dissolving hydroxypropyl beta-cyclodextrin in the sparged water to obtain a hydroxypropyl beta-cyclodextrin solution;
(c) acidifying the hydroxypropyl beta-cyclodextrin solution to a pH of about 1.5 to about 2.0;
(d) dissolving posaconazole in the acidified hydroxypropyl beta-cyclodextrin solution to obtain a posaconazole solution;
(e) adjusting the pH of the posaconazole solution to about 2.3 to about 2.8;
(f) adding water to obtain a final volume;
(g) filling the composition into a container, overlaying the container headspace with nitrogen, and sealing the container;
wherein, after storage at a temperature of about 20° C. to about 32° C. and a relative humidity of about 55% to about 80% for at least 6 months, the composition contains not more than 0.05% by HPLC of deshydroxy posaconazole, contains not more than 0.03% by HPLC of benzylated posaconazole when determined by HPLC method, has total impurities not more than 0.8%, and has coloration not more intense than BY5.

2. The posaconazole liquid composition as claimed in claim 1, wherein the concentration of hydroxypropyl beta-cyclodextrin in the composition ranges from about 280 mg/ml to about 380 mg/ml.

3. The posaconazole liquid composition as claimed in claim 1, wherein the composition further comprises at least one excipient selected from anti-oxidants, chelating agents, pH-adjusting agents, buffering agents or tonicity agents.

4. The posaconazole liquid composition as claimed in claim 3, wherein the chelating agent is sodium edetate.

5. The posaconazole liquid composition as claimed in claim 1, wherein the composition is in the form of a solution for parenteral administration.

6. The posaconazole liquid composition as claimed in claim 2, wherein the composition is stable to dilution when 1 part of the posaconazole liquid composition is diluted to about 30 parts by infusion fluids.

7. The posaconazole liquid composition as claimed in claim 1, wherein the osmolality of the composition ranges from about 200 mOsmol/kg to about 800 mOsmol/kg.

8. The posaconazole liquid composition as claimed in claim 1, wherein the composition, when stored in the container with the claimed amount of posaconazole at a temperature of about 20° C. to about 32° C., for at least 22 months, in an upright orientation or inverted orientation, contains posaconazole not less than about 90% by weight of the amount claimed on the container and contains not more than about 2% by weight of total impurities, at the end of the given storage period.

9. The posaconazole liquid composition as claimed in claim 1, wherein the pH of the posaconazole solution is adjusted from about 2.4 to about 2.7.

10. The posaconazole liquid composition as claimed in claim 2, wherein the concentration of hydroxypropyl beta-cyclodextrin in the composition is about 280 mg/ml.

11. The posaconazole liquid composition as claimed in claim 2, wherein the concentration of hydroxypropyl beta-cyclodextrin in the composition is about 380 mg/ml.

12. A posaconazole liquid composition comprising
(i) posaconazole at a concentration of about 15 mg/ml to about 30 mg/ml in the composition,
(ii) hydroxypropyl beta-cyclodextrin at a concentration of about 200 mg/ml to about 400 mg/ml in the composition, and
(iii) water as a vehicle,
wherein the composition is prepared by dissolving posaconazole in an acidified hydroxypropyl beta-cyclodextrin solution and adjusting the pH of the composition to about 2 to about 4, and the composition is enclosed in a container, wherein headspace of the container is overlayed with a non-oxygen containing gas, wherein, after storage at a temperature of about 20° C. to about 32° C. and a relative humidity of about 55% to about 80% for at least 6 months, the composition contains not more than 0.05% by HPLC of deshydroxy posaconazole, contains not more than 0.03% by HPLC of benzylated posaconazole when determined by HPLC method, and has coloration not more intense than BY6.

13. The composition as claimed in claim 12, wherein the concentration of hydroxypropyl beta-cyclodextrin in the composition ranges from about 250 mg/ml to about 350 mg/ml.

14. The composition as claimed in claim 12, wherein the non-oxygen containing gas is nitrogen.

15. The posaconazole liquid composition as claimed in claim 14, wherein the posaconazole liquid composition after 22 months storage at a temperature of about 20° C. to about 32° C. and a relative humidity of about 55% to about 80% is stable and has coloration not more intense than BY5.

\* \* \* \* \*